(12) United States Patent
Penny

(10) Patent No.: US 11,134,971 B2
(45) Date of Patent: Oct. 5, 2021

(54) WRISTED INSTRUMENT WITH SHARED PITCH AND YAW AXES EXISTING AT THE JAW PIVOT

(71) Applicant: Asensus Surgical US, Inc., Durham, NC (US)

(72) Inventor: Matthew Robert Penny, Holly Springs, NC (US)

(73) Assignee: Asensus Surgical US, Inc., Durham, NC (US)

( * ) Notice: Subject to any disclaimer, the term of this patent is extended or adjusted under 35 U.S.C. 154(b) by 123 days.

(21) Appl. No.: 16/513,710

(22) Filed: Jul. 17, 2019

(65) Prior Publication Data

US 2021/0015513 A1    Jan. 21, 2021

(51) Int. Cl.
*A61B 17/29*        (2006.01)

(52) U.S. Cl.
CPC ...... *A61B 17/29* (2013.01); *A61B 2017/2902* (2013.01); *A61B 2017/2938* (2013.01); *A61B 2017/2939* (2013.01)

(58) Field of Classification Search
CPC .... A61B 2017/2926; A61B 2017/2927; A61B 2017/2929; A61B 2017/2938; A61B 2017/2939; A61B 2034/301; A61B 2034/302; A61B 2034/303; A61B 2034/304; A61B 2034/305; A61B 34/30
See application file for complete search history.

(56) References Cited

U.S. PATENT DOCUMENTS 5,752,973 A * 5/1998 Kieturakis ............. A61B 17/29
                                                    606/205
2016/0262782 A1 * 9/2016 Kalmann ........... A61B 17/2816

* cited by examiner

*Primary Examiner* — Majid Jamialahmadi

(57) ABSTRACT

A surgical instrument includes a shaft and a pair of jaw members disposed on the shaft and extending from an at least partially spherical element. The jaw members are moveable in pitch and yaw relative to the center of the sphere in response to actuation forces applied to a proximal drive mechanism of the instrument. The surgical instrument may include a manually operated handle for manual input of actuation forces by a user, or it may be removably mounted to a drive component of a robotic system such that its proximal drive mechanism is operatively engaged with actuators that generate mechanical output that is transferred to the proximal drive mechanism.

15 Claims, 3 Drawing Sheets

WRISTED INSTRUMENT WITH SHARED PITCH AND YAW AXES EXISTING AT THE JAW PIVOT

BACKGROUND

In laparoscopic and robotic surgery, wristed and articulating instruments provide additional dexterity for the surgeon—enabling access to tissue in small, constrained spaces. Some such instruments have a single pitch joint and a single yaw joint, while others have multiple joints for pitch and yaw. Still other instruments incorporate a combination of yaw pivot and distal end rotation.

Some of the commercially available instruments using discreet joint instruments (single joint for pitch and yaw), are configured such that the pitch and yaw joints share a single axis. This creates a scenario where the distance from the tip of the instrument end effector to the pitch joint is the same as it is to the yaw joint. Instruments where the pitch and yaw joints do not share the same axis will have different distances from the end effector tip to the respective joints. Having the pitch and yaw joint share the same axis offers the advantages that the overall achievable angle is lower than if the axes were separate.

This application describes end effector embodiments that use a shared axis for pitch and yaw joints, but that also position that axis at the jaw pivot. This will enable use of wristed instruments in extremely small workspaces.

DETAILED DESCRIPTION

This application shows and describes end effectors for a surgical instrument. These end effectors are positioned at the distal end of an instrument shaft. The surgical instrument may be configured for manual operation using a proximal drive mechanism in the form of a manually actuated instrument handle at the proximal end of the instrument shaft. Alternatively, for robotically assisted operation, the instrument's proximal drive mechanism receives motion from robotically controlled actuators operating in accordance with surgeon input to a surgical robotic system. In this latter type of configuration, the instrument may be removably mounted to a drive component of the robotic system such that its proximal drive mechanism is operatively engaged with actuators (e.g. electromechanical actuators, or hydraulic/pneumatic actuators) that generate mechanical output that is transferred to the proximal drive mechanism. The drive component may be an arm that supports the instrument and includes the actuators, or it might be some other form of drive component (e.g. a motor pack) that is engaged with the instrument.

Figure 1:
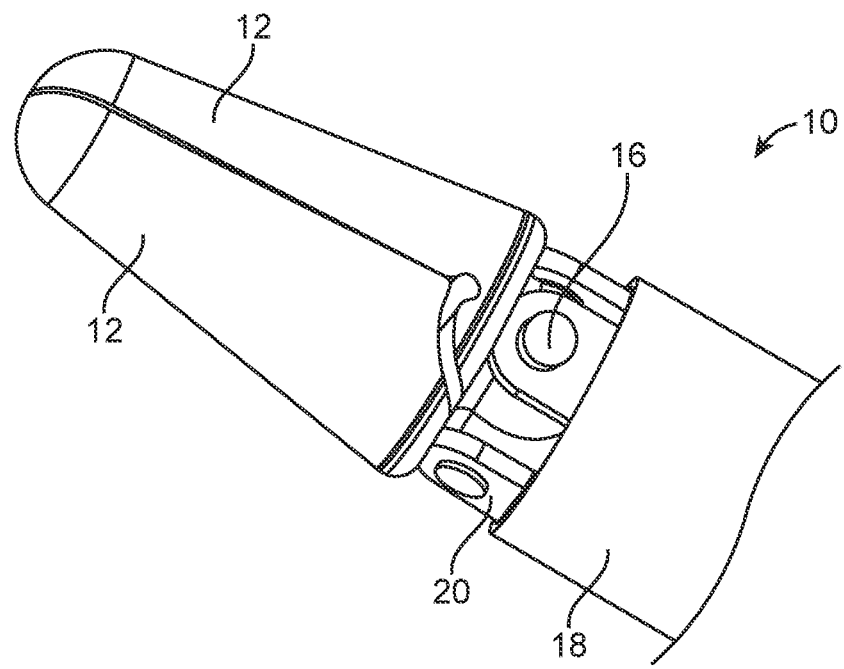
FIG. 1 is a perspective view of an instrument end effector, which uses external pivots.
Figure 2:
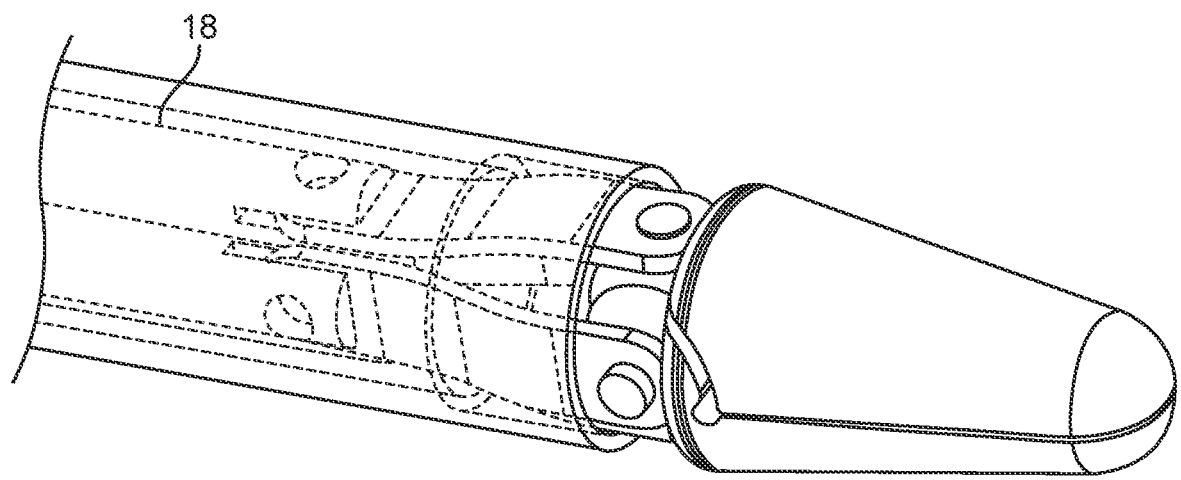
FIG. 2 shows the instrument of FIG. 1 with the shaft made transparent to allow the flatwires to be seen.
Figure 3A:
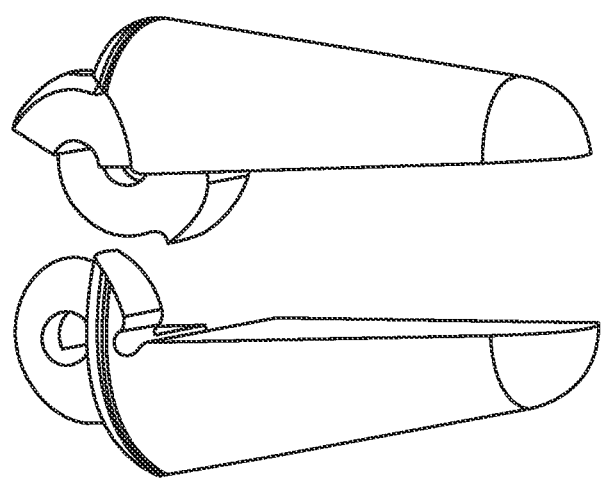
FIGS. 3A-3D are a perspective view, a plan view, a distal end view and a proximal end view, respectively, of the jaw members. In these drawings, the jaw members are separated to allow their features to be move visible.
Figure 3B:
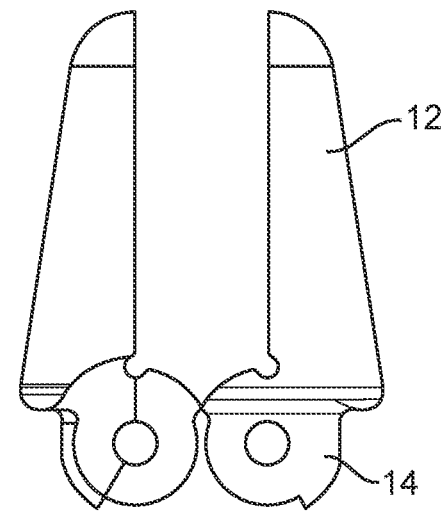
Figure 3C:
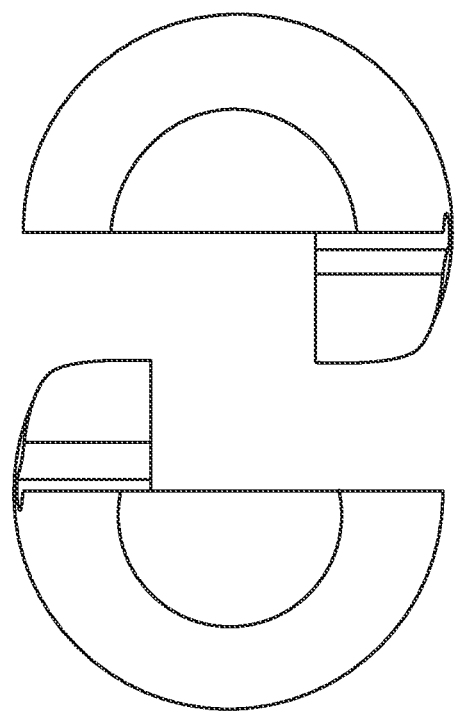
Figure 3D:
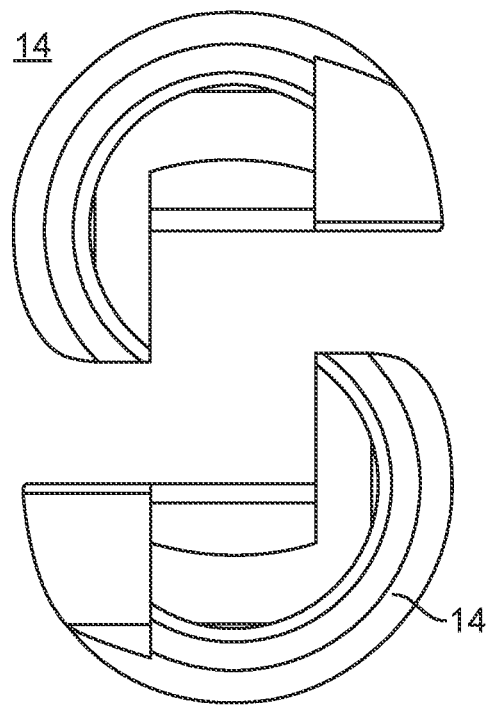

FIG. 1 shows a first embodiment of an instrument 10 having a pair of jaws 12. Each jaw has a base 14 shaped in the form of a portion of a sphere or one half of a sphere. Each base 14 has two pivot pins 16, positioned orthogonal to one another. When the jaws are assembled together, the bases 14 form a sphere (except for the portion from which the jaw members extend) and there are four pins 16 positioned on the same plane, each pin orthogonal to the next.

The shaft 18 of the instrument includes an outer sleeve and four tendons 20 extending from the proximal drive mechanism to the instrument end effector. At the distal end of each tendon, there is a flat wire that extends from the distal side of each tendon to one of the pins 16 on the end effector sphere. The flat wire can pivot both at the pin on the sphere and at the end of the tendon. Alternate embodiments could use a bendable connection between the tendon and the pin.

The flat wire transforms movement of the tendon into movement at the respective pin. The end effector can be articulated in pitch by pushing or pulling on one pair of tendons in opposite directions and articulated in yaw by pushing or pulling on the other pair of tendons in opposite directions. The pitch tendons can also be pushed or pulled in the same direction to open or close the jaw end effector. Additionally, pushing all tendons or pulling all tendons at the same time would extend or retract the end effector from the outer sheath 18 and if the tendons themselves can be rotated relative to the instrument shaft, the end effector may be axially rotated.

Figure 4:
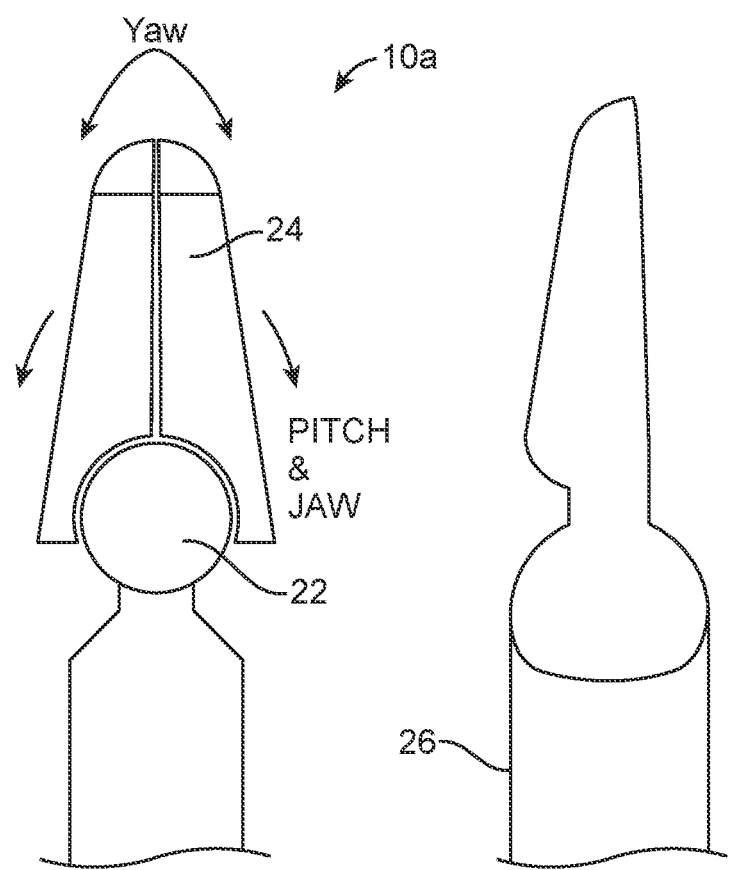
FIG. 4 shows a second embodiment of an instrument end effector, which uses internal pivot points.

A second embodiment 10a of an end effector, shown in FIG. 4, uses an internal ball pivot 22 upon which the jaws of the end effector will rotate. The internal ball 22 is fixed such that each jaw 24 can slide around the ball's outer diameter. The jaws are designed such that assembling them to each other with the ball pivot in between will capture the ball pivot.

The motion of the end effector 10a can be controlled with a similar mechanism to what is described with respect to the first embodiment. Alternatively, as shown in the drawing, the end effector can have two cables 26, each wrapped around a separate jaw such that the center of each cable is fixed to each jaw. The ends of each cable are terminated into adjacent tendons that extend from the distal end of the instrument shaft to the proximal drive mechanism. Pulling on one side of each cable attached to a jaw will move that jaw in pitch, while pulling on both cables for a given jaw will move that jaw in a yaw direction.

What is claimed is:

1. A surgical instrument comprising:
    a shaft and a pair of jaw members disposed at a distal end of the shaft, wherein each of the jaw members include a partially spherical base, and wherein the bases are positioned together to form an at least partially spherical element, the jaw members extending from said at least partially spherical element, and moveable in pitch and yaw relative to a center of the at least partially spherical element;
    wherein each of the bases has two pivot pins positioned orthogonal to one another and an actuation tendon coupled to each of the pivot pins.

2. The surgical instrument of claim 1, wherein applying forces to a first pair of the actuation tendons in opposite direction moves the jaw members in pitch about a pitch axis.

3. The surgical instrument of claim 2, wherein applying forces to a second pair of the actuation tendons in opposite direction moves the jaw members in yaw about a yaw axis, wherein the pitch axis and the yaw axis are orthogonal to one another.

4. The surgical instrument of claim 1, wherein the jaw members form an end effector, and wherein simultaneously pushing or pulling the actuation tendons extends or retracts the end effector relative to the shaft.

5. The surgical instrument of claim 1, wherein the jaw members form an end effector, and wherein rotating the actuation tendons about a longitudinal axis of the shaft rotates the end effector relative to the shaft.

6. The surgical instrument of claim 1, wherein each of the actuation tendons include a flat wire at its distal end, each of the flat wires coupled to the corresponding pin.

7. The surgical instrument of claim 1, wherein the surgical instrument includes a handle manually operable to apply force to the tendons.

8. The surgical instrument of claim 1, wherein the surgical instrument is removably attachable to a drive component of a robotic system, wherein the drive component is movable in response to user input commands to the robotic system to deliver force to the actuation tendons.

9. A method of using a surgical instrument comprising:
providing the surgical instrument having a shaft and a pair of jaw members disposed at a distal end of the shaft wherein each of the jaw members include a partially spherical base, the partially spherical bases of the jaw members are positioned together to form an at least partially spherical element and wherein each of the bases has two pivot pins positioned orthogonal to one another and an actuation tendon coupled to each of the pivot pins; and
causing the jaw members to move in pitch and yaw relative to a center of the at least partially spherical element by selectively applying force to the actuation tendons.

10. The method of claim 9, wherein the method includes applying forces to a first pair of the actuation tendons in opposite directions to move the jaw members in pitch about a pitch axis.

11. The method of claim 10, wherein the method includes applying forces to a second pair of the actuation tendons in opposite directions to move the jaw members in yaw about a yaw axis, wherein the pitch axis and the yaw axis are orthogonal to one another.

12. The method of claim 11, wherein the jaw members form an end effector, and wherein the method includes simultaneously pushing or pulling the actuation tendons to extend or retract the end effector relative to the shaft.

13. The method of claim 11, wherein the jaw members form an end effector, and wherein the method includes rotating the tendons about a longitudinal axis of the shaft to rotate the end effector relative to the shaft.

14. The method of claim 11, wherein the method includes simultaneously pushing or pulling the first pair of the actuation tendons in the same direction to open or close the jaw members.

15. The method of claim 10, wherein the method includes removably mounting the surgical instrument to a drive component of a robotic surgical system, and wherein the step of selectively applying force to the actuation tendons comprises causing the drive component to deliver force to the actuation tendons in response to user input commands of the robotic surgical system.

* * * * *